United States Patent
Fleig et al.

(10) Patent No.: US 8,175,675 B2
(45) Date of Patent: May 8, 2012

(54) DEFORMABLE MARKER DEVICE

(75) Inventors: Oliver Fleig, Baldham (DE); Ingmar Hook, Feldkirchen (DE)

(73) Assignee: Brainlab AG, Feldkirchen (DE)

(*) Notice: Subject to any disclaimer, the term of this patent is extended or adjusted under 35 U.S.C. 154(b) by 793 days.

(21) Appl. No.: 12/030,228

(22) Filed: Feb. 13, 2008

(65) Prior Publication Data
US 2008/0194948 A1 Aug. 14, 2008

Related U.S. Application Data

(60) Provisional application No. 60/891,794, filed on Feb. 27, 2007.

(30) Foreign Application Priority Data

Feb. 13, 2007 (EP) ................................. 07002992

(51) Int. Cl.
*A61B 5/05* (2006.01)
(52) U.S. Cl. ..................................................... 600/407
(58) Field of Classification Search .............. 600/407, 600/414, 420, 426, 431, 432, 436, 2–4, 7, 600/26.6, 36, 424, 458; 604/53, 265; 424/423; 606/194, 196, 191, 198; 623/1, 2, 12, 1.15, 623/1.34, 23.7, 23.71
See application file for complete search history.

(56) References Cited

U.S. PATENT DOCUMENTS

| 3,547,121 A | 12/1970 | Cherry |
| 3,830,414 A * | 8/1974 | Caprielian ................ 224/175 |
| 4,319,136 A | 3/1982 | Jinkins |
| 5,193,106 A | 3/1993 | DeSena |
| 6,174,330 B1 * | 1/2001 | Stinson .................... 623/1.34 |
| 2005/0004581 A1 | 1/2005 | Astrom |
| 2006/0173264 A1 | 8/2006 | Jansen |

FOREIGN PATENT DOCUMENTS
EP 1 611 862 1/2006

OTHER PUBLICATIONS

U.S. Appl. No. 12/029,716, filed Feb. 12, 2008 titled "Determining a Three-Dimensional Model of a Rim of an Anatomical Structure".

* cited by examiner

*Primary Examiner* — Tse Chen
*Assistant Examiner* — Elmer Chao
(74) *Attorney, Agent, or Firm* — Renner, Otto, Boisselle & Sklar, LLP

(57) ABSTRACT

A deformable marker device for adapting to a human or animal body includes a plurality of marker elements, and a connecting device that connects at least some marker elements of the plurality of marker elements to each other. The connecting device enables the at least some marker elements to be moved relative to each other so as to adapt a shape of the marker device to a course of a curved surface.

16 Claims, 2 Drawing Sheets

DEFORMABLE MARKER DEVICE

RELATED APPLICATION DATA

This application claims priority of U.S. Provisional Application No. 60/891,794 filed on Feb. 27, 2007, which is incorporated herein by reference in its entirety.

FIELD OF THE INVENTION

The present invention relates to medical markers and, more particularly, to a deformable marker device that can be adapted to a surface of a human or animal body and/or placed onto said body.

BACKGROUND OF THE INVENTION

In medical navigation, markers are typically attached to an object to be tracked. These medical markers may be passive markers (e.g., light reflecting markers), active markers (e.g., light generating markers), or magnetic markers (e.g., coils). By tracking a location of the marker, the location of the object attached thereto also can be tracked.

Conventional marker devices are not deformable. Instead, the individual marker elements of the marker device have a fixed position relative to each other, such as is for example known from so-called reference stars.

SUMMARY OF THE INVENTION

A deformable marker device in accordance with the present invention preferably comprises a plurality of marker elements connected to each other, wherein the marker elements can be moved relative to each other. The markers can be configured such that they are impermeable to waves and/or radiation used in medical analysis (e.g., x-ray radiation), reflect said waves and/or radiation (e.g., infrared light or ultrasound) or emit waves and/or radiation themselves (e.g., light or infrared light). Images obtained using such imaging techniques (x-ray imaging, infrared light, ultrasound, etc.) are referred to herein as a medical image. The interaction between the marker elements and the waves and/or radiation can be verified by detection devices (e.g., x-ray radiation detectors or light-sensitive sensors).

The deformability of the marker device is preferably achieved using a connecting means that connects the marker elements. The connecting means, for example, can be flexible (e.g., a material) and/or jointed (e.g., a mechanical joint connection between the marker elements). The distance between at least some of the marker elements can be variable. This is the case, for example, if the connecting means is a flexible cloth. The connecting means can, but need not, be elastic. The term "can be moved" means that the marker spheres can be moved relative to each other by a person, without a tool, by applying a minor or normal force, without destroying or damaging the connecting means.

The marker device is preferably used to simplify the determination of a three-dimensional model of an anatomical structure from two two-dimensional images. In particular, the marker device can simplify the determination of correspondence points, wherein correspondence points can be used to determine the three-dimensional position of object points of a structure from two two-dimensional images of the structure from two different directions (in accordance with the principles of epipolar geometry). In particular, the marker device in accordance with the invention can enable the determination of a so-called fundamental or essential matrix (or also localization matrix), which describes properties of the geometry forming the basis of the at least two images. Further information regarding epipolar geometry and determining correspondence points can be found in co-pending U.S. application Ser. No. 12/029,716 filed on Feb. 12, 2008 and titled "Determining a Three-dimensional Model of a Rim of an Anatomical Structure", the contents of which is hereby incorporated by reference in its entirety.

Conventional localization techniques for determining a localization matrix use rigid objects for which the geometric relationship between the markers is exactly known. A deformable, in particular flexible marker device can be used in accordance with the invention as a localizer, wherein in accordance with one embodiment, the marker elements are visible in x-ray images. For a localization method, in particular for determining the localization matrix in accordance with the principles of epipolar geometry, the relative position between the marker elements should remain the same in the images. Knowledge of the exact geometric relationship between all of the marker elements is not compulsory.

A localization algorithm can be used to determine the localization matrix, for example, by extracting relative camera movement from pairs of correspondence points, as is known from the field of "stereovision". Such algorithms are known and can be used to extract three-dimensional information from video scenes (i.e., a sequence of images recorded by a moving camera), satellite images or images achieved by a specific stereo configuration (e.g., two cameras aligned in parallel that simultaneously capture images). Examples of such algorithms include the eight-point algorithm (Longuit-Higgins) or the five-point algorithm (Stewénius/Engels/Nistér), which is preferably used. If the algorithms are used for video recordings or other "actual" images captured by a conventional lens system, image features such as edges and grey-color values are typically used to automatically find the matching correspondences (e.g., an edge of a traffic sign in a first image will correspond to the same edge in a second image). A different approach is preferred for x-ray images, since edge information is usually difficult to determine or unreliable because the images have a translucent or transparent property and/or because organic objects are rounded. The latter is in contrast to typical video recordings, which, for example, show buildings or cars that have identifiable edges.

In accordance with an aspect of the invention, marker elements are inserted into the image so as to artificially produce "prominent" image portions that can be used as correspondence points. In particular, this enables the correspondence points to be automatically detected.

When analogously using the marker device (e.g., the marker device is attached or adapted to a human or animal body), at least some (preferably most) of the marker elements are preferably spaced apart from each other, while the marker elements also can be moved relative to each other. The connecting means can be configured such that the marker elements assume predetermined positions when the marker device is spread out. The marker device preferably is designed flat.

Preferably, at least two of the marker elements are held at a fixed distance by the connecting means. To this end, the connecting means can be stiffened between these two marker elements or can comprise a rigid connecting member having a marker element attached to each of its ends. The known, fixed distance is preferably used to calibrate, in particular gauge, the geometry of the imaged object. The localization matrix can be gauged in this way. The distance between the remaining marker elements can be variable.

The markers preferably have differing shapes and/or sizes. There can be at least two groups of markers, wherein the shape and/or size within the group is the same and the markers belonging to different groups differ in shape and/or size. Preferably, the at least two markers that are fixedly spaced apart from each other differ in shape and/or size from the remaining markers, or belong to a group of markers that differ in shape and/or size from the majority of the marker elements.

The deformable marker device is preferably wound or attached at least partially around a part of a human or animal body. This means that when said part of the body is recorded, a first portion of the marker elements are then situated in front of the part of the human or animal body from the viewing direction of the imaging apparatus, and a second portion of the marker elements are situated behind the part of the human or animal body. The marker elements are preferably characteristically different in their shape, size and/or arrangement, such that it is possible to tell from the image which marker elements are in front of the part of the body and which are behind the part of the body. For instance, a different arrangement is given if a location of a foreground marker element relative to neighboring foreground marker elements differs from a location of a background marker element relative to neighboring background marker elements. The surrounded part of the body is also referred to as the "inner region", since it lies within the region surrounded by the marker device. A characteristic arrangement, for example, would be an arrangement in lines, wherein the upper and lower line are in the foreground and the middle line is in the background. Alternatively or additionally, the marker elements in the foreground, for example, may be arranged in a zigzag shape, while the marker elements in the background may be arranged linearly. Another alternative would be for the marker elements arranged in the foreground to be cube-shaped, while the marker elements arranged in the background can be spherical, resulting in square or round areas in the image that allow the markers to be identified as foreground markers or background markers. Lastly, the marker elements arranged in the background, for example, can have a significantly different size relative to the marker elements arranged in the foreground.

The connecting means also can be designed such that movement of the marker elements in a first direction is easier than movement of the marker elements in a direction perpendicular to the first direction. The marker device, for example, can be designed such that it is easy to deform the marker device into the shape of a cylindrical cloak, while a relative movement of the marker elements in the direction of the cylindrical axis requires a greater force to be applied. This increases the stability of the marker device.

BRIEF DESCRIPTION OF THE DRAWINGS

The forgoing and other features of the invention are hereinafter discussed with reference to the drawing.

DETAILED DESCRIPTION

Figure 1:
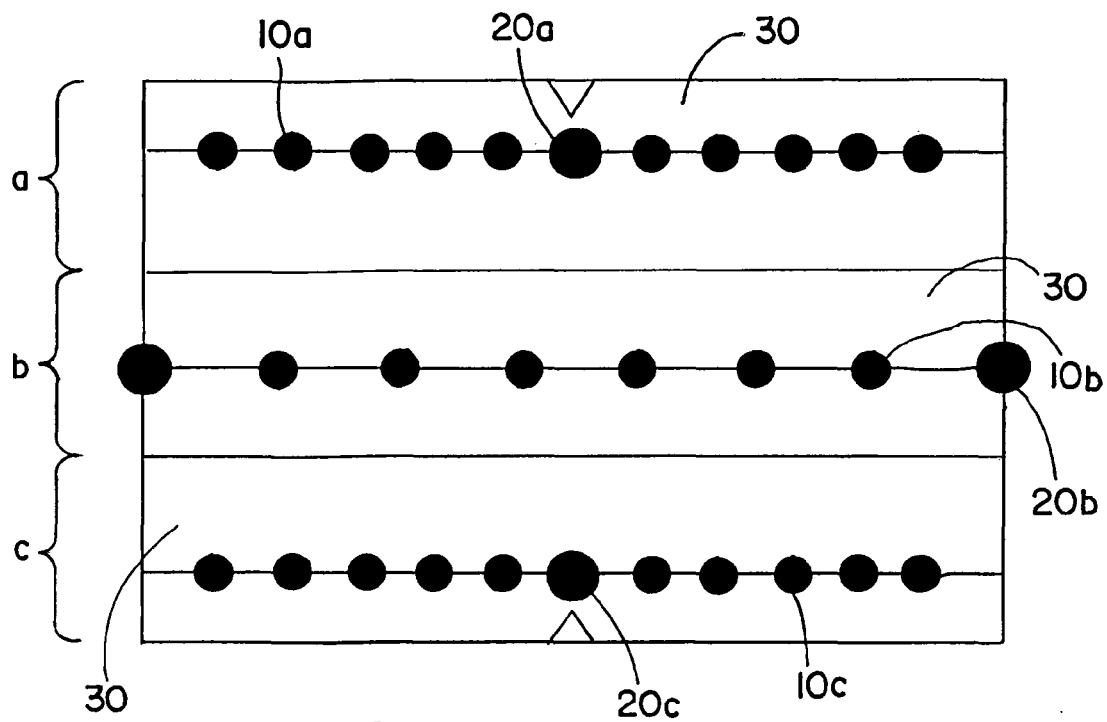
FIG. 1 shows an exemplary arrangement of marker elements in a marker device in accordance with the invention.

FIG. 1 shows a schematic arrangement of exemplary marker elements, which are shown as black circular areas 10 and 20 attached along strips a, b and c. The marker elements are preferably designed as marker spheres that are divided into two groups of different diameters. In the given example, the diameters measure 5 millimeters and 9 millimeters, and the marker spheres along a strip are each spaced apart by 2.5 centimeters. The sizes (diameters) of the marker elements can be arbitrarily selected. They can be larger than 1 millimeter and smaller than 3 centimeters. The distance between the marker elements within a strip can be larger than 2 millimeters and smaller than 10 centimeters. In the given example, the distance between the center points of the marker elements in the upper strip a and lower strip c measures 16.7 centimeters. This is purely by way of example. The distance can be greater than 3 centimeters and less than 30 centimeters. The outer dimensions of the arrangement shown in FIG. 1 measure approximately 20×30 centimeters and are also purely by way of example.

In accordance with one embodiment of the invention, marker elements are arranged flat and connected via a flat cloth 30. The marker elements can be attached to predetermined positions on the flat cloth. Alternatively or in addition to cloth 30, the marker elements may be connected to one another via a mechanical joint 31 (e.g., a hinge joint or other joint that enables movement in a first direction, but not in a direction perpendicular to the first direction, etc.). A hinge joint, for example, can include connecting elements (e.g., a first part and a second part) that are coupled together by a common shaft or the like. Such joints are well know and will not be further described herein.

The cloth comprising the marker elements can be wound around a part of the body of a (human or animal) patient in the manner of a kidney belt or in the manner of a cuff. The flat cloth 30 shown in FIG. 1, for example, can be shaped into a cylindrical cloak, wherein the strips a and c should be on the front half of the cylindrical cloak, while the strip b should be on the rear half of the cylindrical cloak. The cloth shown in FIG. 1 thus can be double-layered, wherein the strips a and c form part of the front layer and the strip b forms part of the rear layer. In other words, the strips a and c represent a view of the cuff-shaped marker device from the front, and the strip b represents a view from the rear.

Figure 2:
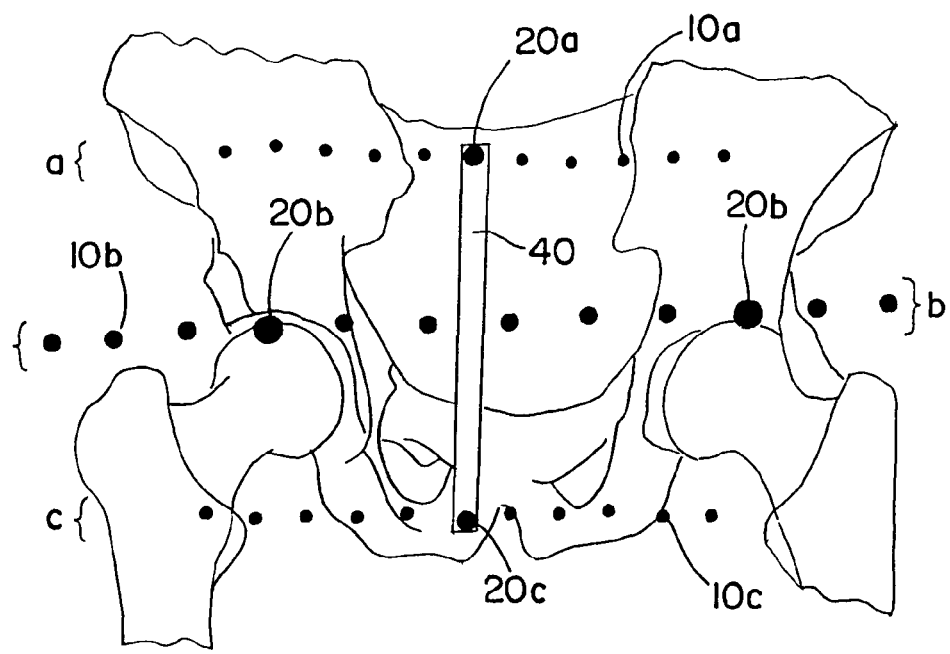
FIG. 2 shows an exemplary x-ray recording of a pelvis, around which a marker device in accordance with the invention has been wound.

FIG. 2 is an x-ray recording of a pelvis. In front of the x-ray recording, a belt configured in accordance with the device of FIG. 1 has been wound around the patient's pelvis and attached to the human body (e.g., by a waistband, buttons and/or by designing the cloth to be elastic) and/or is held on the human body by tension. The marker elements 10 and 20, which are visible in the x-ray recordings, can again be seen as black circles in FIG. 2 in their characteristic arrangement known from FIG. 1. They are arranged along the lines a, b and c, which correspond to the strips a, b and c in FIG. 1. The lines are clearly identifiable, since the distance between the marker elements within a line is preferably less than the distance between the lines. Further, the strips a, b and c are arranged such that marker elements do not lie one directly behind the other when the device is formed as a closed area (e.g., when formed as an area resembling a cylinder or elliptic cylinder, or other shape that conforms to an outer surface of the patient's body).

The larger marker spheres 20 are conspicuous and clearly distinguished from the smaller marker spheres 10. A rod 40 also can be seen, which is not shown in FIG. 1. The rod 40 preferably consists of a material that is at least partially permeable to x-rays, e.g., a plastic such as PVC. The rod 40 is preferably designed rigid and defines a fixed distance between two marker spheres situated on the same side of the part of the body. In the given example, this is the connection between the two large marker spheres 20a and 20c situated on the front side of the pelvis. Using a spacer 40 allows the localization matrix to be calibrated or gauged in terms of size.

Figure 3:
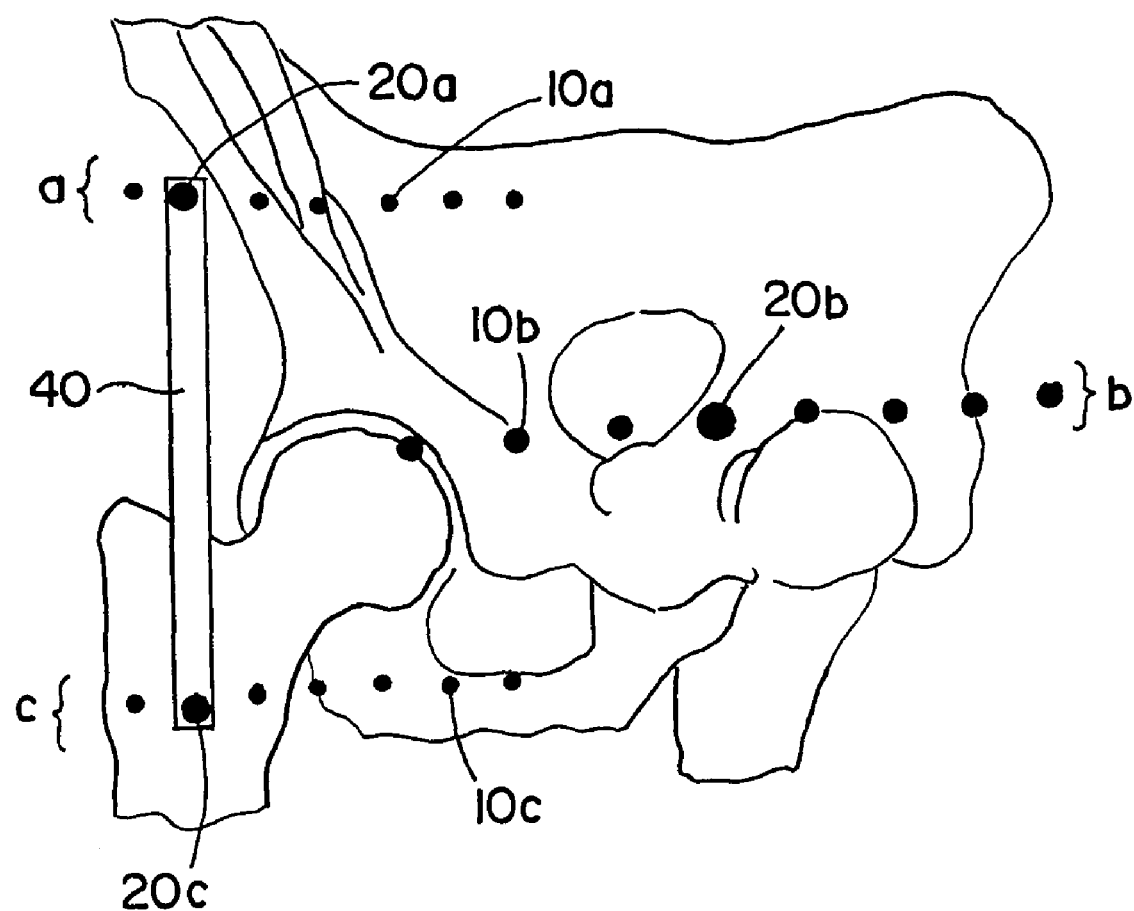
FIG. 3 shows another exemplary x-ray recording under the same conditions as FIG. 2 but from a different direction.

While FIG. 2 shows a frontal recording of the pelvis, FIG. 3 is an x-ray recording taken from the view of the observer from obliquely front-right. In other words, the right-hand hip joint has been rotated forwards while the recording apparatus remains stationary.

The marker spheres corresponding to each other in FIGS. 2 and 3 can be easily determined. The large marker spheres 20 can serve as starting points. The large marker sphere 20a, for example, has five small marker spheres 10a located to its right. Each of the identical marker spheres have been provided with reference signs in FIGS. 2 and 3. The left-hand marker sphere of the two large marker spheres 20b in FIG. 2 can be seen in the middle row b in FIG. 3. The large marker spheres 20a and 20c are shown in both images. The translucently visible spacer 40 provides an additional identification aid.

Due to the relative shift in position between the marker spheres, it is possible when comparing FIGS. 2 and 3 to determine the different recording geometry in each case. As can be seen, the middle group of markers (10b, 20b) is shifted to the right from FIG. 2 to FIG. 3 relative to the upper (10a, 20a) and lower (10c, 20c) group of markers. This is due to the fact that the marker spheres of the strip b are behind the imaged pelvis, while the marker spheres of the strips a and c are in front of the imaged pelvis. Changing the imaging direction appears to shift the position of the marker spheres in the images. In reality, however, the marker spheres are stationary relative to the anatomical structure while the two x-ray recordings are taken, since the marker device is fixedly strapped to the patient.

The changed imaging direction can be determined from the relative shift from FIG. 2 to FIG. 3. For example the imaging direction can be determined based on the shift of the spheres 20b relative to the spheres 20a and 20c, and on the known distance between the marker spheres 20a and 20c. The distances between the marker spheres within a group or "line" also can be adduced, particularly if the cloth is a flexible but inelastic cloth.

In summary, it is possible to determine information on the change in the imaging conditions from image to image, in particular on the change in the imaging direction, from the images of the marker elements. The so-called essential matrix or localization matrix can be determined, which contains essential information on the imaging geometry that changes from image to image. If this matrix is determined, then it is possible to produce three-dimensional models of the imaged anatomical structure from the two images, based on the principle of epipolar geometry.

As shown in FIG. 2, the middle row b of markers contains two large marker spheres 20b. This is only one example embodiment. In accordance with another embodiment, one larger marker sphere is also sufficient. Arranging the larger marker spheres 20b to the left and right of the center lying at the rod 40 simplifies handling. In particular, the belt does not have to be rotated about an axis running normal to and through the center in FIG. 1, depending on whether the left-hand or right-hand side of the anatomical structure is to be more precisely examined.

If a recording protocol is defined for the x-ray recording in which the part to be treated is to be rotated forwards or backwards, then it is possible to automatically determine which side is the side to be treated from the shift in the rows of marker spheres relative to each other. In other words, due to the recording protocol, the side which is to be treated can be deduced from the polarity of the rotational angle between the two images, as determined from the images. This can be utilized within the framework of an evaluation software.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A deformable medical marker device adaptable to a body part so as to surround the body part, comprising:
    a plurality of medical marker elements;
    a connecting device that connects at least a first subset of medical marker elements within the plurality of medical marker elements to each other, a second subset of medical marker elements within the plurality of medical marker elements to each other, and a third subset of medical marker elements within the plurality of medical marker elements to each other, the first, second and third subsets each comprising a plurality of markers, each of the plurality of markers belonging to only one of the first, second or third subsets,
    wherein the connecting device enables at least some medical marker elements of the first subset to be moved relative to each other, at least some medical marker elements of the second subset to be moved relative to each other, and at least some medical marker elements of the third subset to be moved relative to each other, said relative movement performed without detaching the marker elements from the connecting device so as to adapt a shape of the marker device to a contour of a curved surface of the body part and to surround the body part while remaining connected to each other by the connecting device, and wherein each of the first, second and third subsets comprise a predetermined arrangement, and
    wherein the plurality of marker elements are arranged such that when an imaging device obtains a medical image of the deformable marker device surrounding the body part, it can be determined from the medical image whether a marker element of the plurality of marker elements is in front of the body part or behind the body part relative to the imaging device; and
    a rigid connecting device configured to maintain a fixed distance between at least one marker element of the first subset and at least one marker element of the third subset of the plurality of marker elements as the deformable marker device is deformed at a point directly adjacent to the rigid connecting device.

2. The deformable marker device according to claim 1, wherein at least one marker element arranged to be in a foreground of the medical image is different in arrangement, size or shape from at least one marker element arranged to be in a background of the medical image.

3. The deformable marker device according to claim 1, wherein the at least two marker elements exhibit a shape and/or size that differs from other marker elements of the plurality of marker elements.

4. The deformable marker device according to claim 1, wherein the fixed distance between the at least two marker elements is adjustable.

5. The deformable marker device according to claim 1, wherein a first group of marker elements of the plurality of marker elements exhibit a shape and/or size different from a second group of marker elements of the plurality of marker elements.

6. The deformable marker device according to claim 1, wherein the plurality of marker elements are arranged such that a first group of marker elements of the plurality of marker elements do not obscure a second group of marker elements of the plurality of marker elements when viewing the deformable marker device in a direction normal to a surface of the deformable marker device.

7. The deformable marker device according to claim 6, wherein the first group of marker elements and the second set of marker elements do not lie one directly behind the other.

8. The deformable marker device according to claim 1, wherein the shape of the marker device is formed as a cylinder or an elliptic cylinder.

9. The deformable marker device according to claim 1, wherein the curved area surrounds an inner region, and when viewing the inner region from a first viewing direction the first group of marker elements are in front of the inner region and the second group of marker elements are behind the inner region, and wherein an arrangement, size and/or shape of the first group of marker elements characteristically differs from an arrangement, size and/or shape of the second group of marker elements.

10. The deformable marker device according to claim 9, wherein the arrangement of the first group of marker elements and the second group of marker elements characteristically differs such that when viewing the deformable marker device in a direction normal to a surface of the deformable marker device, the first group of marker elements are sequentially arranged to form a first line, and the second group of marker elements are sequentially arranged to form a second line, wherein the first line is spaced apart from the second line.

11. The deformable marker device according to claim 1, wherein the connecting device comprises a flexible material and/or a mechanical joint connection.

12. The deformable marker device according to claim 11, wherein the mechanical joint connection comprises connecting elements that connect the marker elements to each other to form a joint.

13. The deformable marker device according to claim 12, wherein a length of the flexible material or of the connecting elements between the marker elements is constant.

14. The deformable marker device according to claim 13, wherein the flexible material or mechanical joint connection is configured such that a force required to move the marker elements in a plane is less that a force required to move the marker elements in a direction perpendicular to the plane.

15. The deformable marker device according to claim 1, wherein the plurality of markers are arranged as a plurality of marker groups, wherein a spacing of markers within one marker group differs from a spacing of markers in another marker group.

16. The deformable marker device according to claim 15, wherein the plurality of marker groups comprise at least three marker groups.

* * * * *